United States Patent
Senders

[11] 4,181,408
[45] Jan. 1, 1980

[54] VISION COMPENSATION

[76] Inventor: John W. Senders, 1076 Rutherford Rd., R.R. 2, Maple, Ontario, Canada, L0J 1E0

[21] Appl. No.: 857,430

[22] Filed: Dec. 5, 1977

[51] Int. Cl.² .......................... C02C 7/02; A61B 3/14; G02C 7/06
[52] U.S. Cl. ..................... 351/159; 351/41; 351/7; 350/180; 351/168
[58] Field of Search ............ 351/41, 159, 168, 7, 351/163; 350/179, 180, 355, 356, 357

[56] References Cited
U.S. PATENT DOCUMENTS

| | | | |
|---|---|---|---|
| 1,269,422 | 6/1918 | Gordon | 351/41 |
| 2,576,581 | 11/1951 | Edwards | 351/41 |
| 2,642,776 | 6/1953 | Boeder | 351/41 |
| 3,379,885 | 4/1968 | Nork | 351/7 UX |
| 3,598,479 | 8/1971 | Wright | 351/41 |
| 3,614,215 | 10/1971 | Mackta | 351/159 |
| 3,630,603 | 12/1971 | Letter | 351/163 |

*Primary Examiner*—John K. Corbin
*Assistant Examiner*—Rodney B. Bovernick

[57] ABSTRACT

A vision compensation system includes a lens receiving frame with a pair of lens members, at least one of which has variable optical compensation capabilities. Carried by the frame are means for producing a signal as a function of the relative angular positions of the eyes of the wearer and means responsive to that signal for changing the optical characteristics of the variable lens to provide compensation for impaired accommodative capacity of the wearer's eye.

16 Claims, 5 Drawing Figures

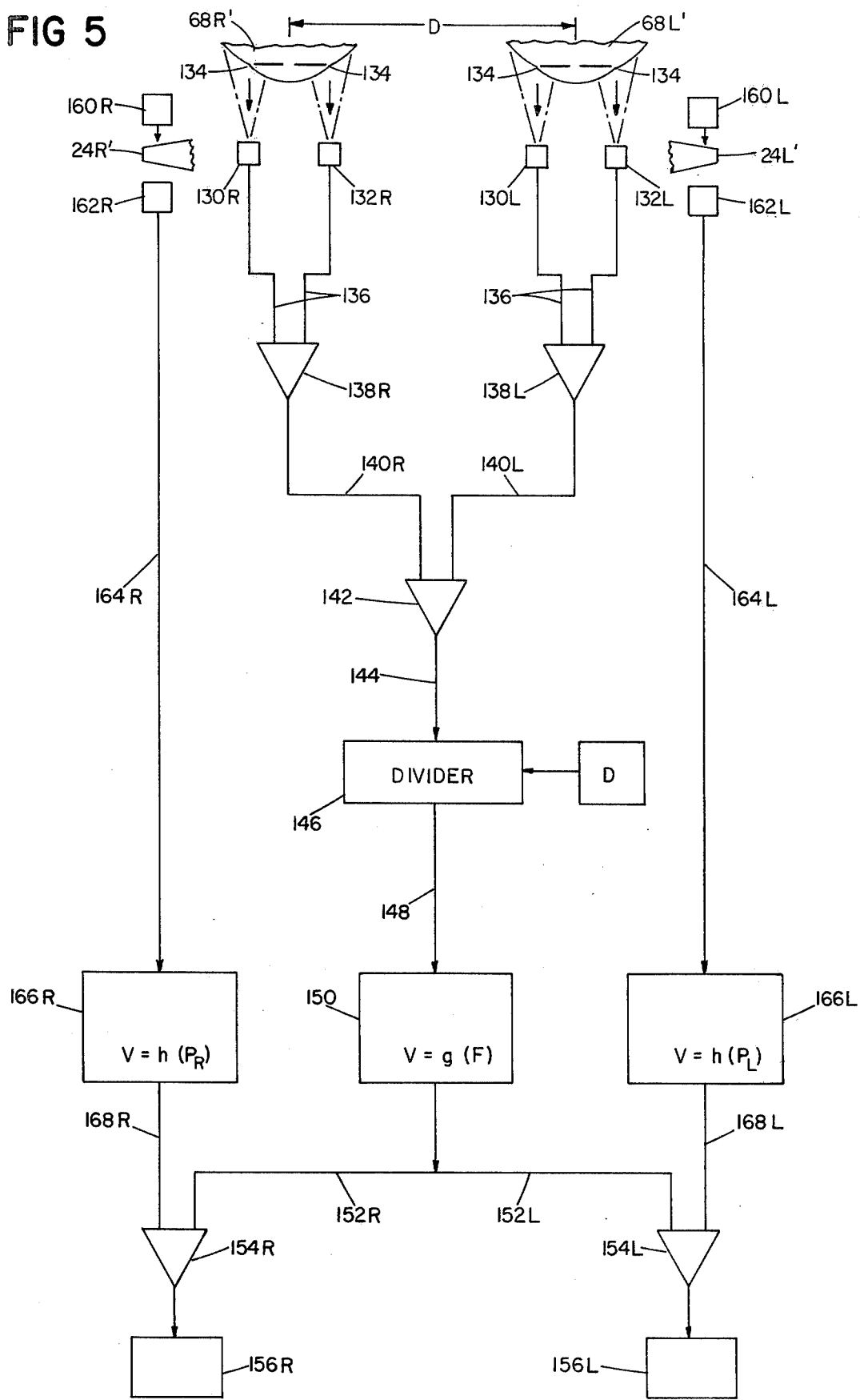

VISION COMPENSATION

This invention relates to adaptively controlled vision compensation systems for ophthalmic purposes.

As a human being increases in age, frequently there is a progressive decline in the ability of the human eye to vary the focal length of the lens. This may result in difficulty in viewing near or distant objects, a condition known as presbyopia. Individuals usually cope with this disability through the use of bifocal, trifocal or polyfocal lens. For many tasks such as automobile driving, dentistry, watch repair and the like, there are frequent shifts in visual attention between near and far points. Also, and particularly at close range, the viewing of the object being observed may differ significantly between the right and left eyes depending on the detail to be seen and the degree of natural accommodation remaining to the viewer. Under these latter conditions, compensation of the two eyes has to be different for best viewing. In a particular instance, an aging aircraft pilot might require zero correction for external world view, a correction of about 1.3 diopters for viewing an instrument panel at a distance of 0.75 meter, and a correction of about 3.3 diopters for reading a fine detail of a map at a distance of about 0.3 meter. While trifocal lens will easily provide these corrections, there is always a resultant limitation of the available fields of view, and depending on the degree of remaining accommodative capacity, there will be loss of visual capacity at some intermediate distances. An even more extreme problem confronts the post-operative cataract patient who has no accommodative capacity.

In accordance with the invention, a vision compensation system is provided that includes a support frame adapted for wearing with at least one optical member which has variable optical compensation capabilities. Carried by the frame are means for producing a signal as a function of the relative angular positions of the eyes of the wearer and means responsive to that signal for changing the optical characteristics of the variable member to provide compensation for impaired accommodative capacity of the wearer's eye.

In a preferred embodiment, the vision compensation system includes adjusting means manipulatable by the fingers of the wearer, while the vision compensation system is being worn, for varying the optical characteristic of the lens. That embodiment also includes means carried by the support frame for sensing the variable optical characteristic of a lens and providing a signal representative of that characteristic and feedback means responsive to that signal for adjusting that optical characteristic.

Among the optical characteristics of a lens that may be varied are lens shape and index of refraction. A variable lens can use forces or movement of one or more lens elements in various forms, to accomplish the desired change in focal length. Similarly, various sensor arrangements may be used for sensing eye position and for the variable optical characteristic. For example, eye position sensing may be accomplished with contact lens like members bearing small mirrors, wire loops, blacks spots, on the edge, magnetic particles or the like; by sensing a voltage change due to eye rotation; or by sensing deformation force in soft contact lenses worn by the user. In a lens system of variable focal length type, for example, the optical characteristic sensor might sense deformation of a lens component or a change in index of refraction. The control system responsive to the eye position signal may control a single optical member or two optical members, either jointly or with different compensation for each optical member depending on factors such as the needs of the user and cost considerations. Control systems may process signals in analog form, in digital form or in a combination of analog and digital form. Vision compensation systems in accordance with the invention may incorporate either closed loop or open loop type control. In systems which include manually manipulatable optical characteristic adjusting means, a manually manipulatable element may control one or both lenses and may be, for example, a rotatable or reciprocal element carried by a temple bow or an electrical switch on a temple bow or remote therefrom that controls the application of power to an optical characteristic drive.

In a particular embodiment, the vision compensation system includes a frame of conventional spectacle configuration that carries two lenses of separately variable focal length. Also carried by the spectacle frame are sources of infrared radiation for illuminating the eyes of the wearer, sensor arrays tuned to the infrared radiation wavelength for providing signals indicating the angular position of the junction between the sclera and the iris, and lens sensors that provide signals indicating actual focal length settings of the two individual lens systems. The control circuitry has two modes of operation, a manual or calibration mode, and an automatic mode. In the calibration mode the focal length of each lens is manually adjusted, and data words representative of a series of eye positions and corresponding focal length settings of each lens for satisfactory user accommodation are stored in three correlated memory register tables. In the automatic mode, the vision compensation system adjusts the focal lengths of the two lenses as a function of angular eye position of the user to provide vision compensation for improved viewing of near and far objects with automatic control that utilizes the stored coordinated data words and feedback signals from the lens sensors.

Other features and advantages of the invention will be seen as the following description of particular embodiments progresses, in conjunction with the drawings, in which:

FIG. 5 is a diagram of another embodiment of a vision compensation system in accordance with the invention.

DESCRIPTION OF PARTICULAR EMBODIMENTS

Figure 1:
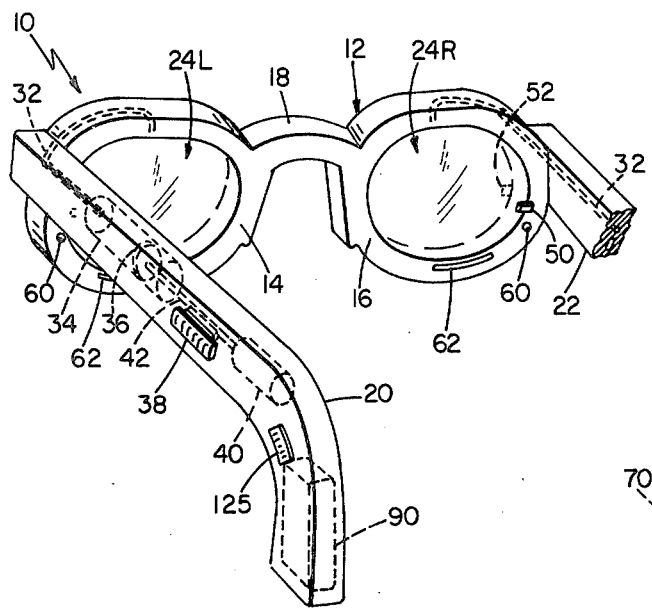
FIG. 1 is a diagrammatic perspective view of a vision compensation system in accordance with the invention with parts broken away.

With reference to FIG. 1, there is shown spectacles 10 comprising a frame 12 having two spaced lense mounting portions 14, 16 connected by bridge portion 18. Extending rearwardly from frame 12 are two temple bows 20, 22. Supported within each frame portion 14, 16, is a variable focus lens unit 24, each of which may be of the type shown in U.S. Pat. No. 3,598,479. Each lens 24 includes a front component 26 in the nature of a conventional spectacle lens and a rear component 28 in the form of a thin sheet of glass, spaced to defined chamber 30 into which a working liquid may be pumped or withdrawn to thereby appropriately change the curvature of the rear lens component 28 and change the focal length of lens system 24. The working liquid is supplied to the lens system chambers 30 by means of passages 32 in the frames 14, 16 which extend to reservoirs 34 in the temple bows 20, 22. A piston 36 in each bow pumps the working liquid in reservoir 34 into and from the lens system and may be reciprocated either by manual drive member 38 or power drive 40 via piston shaft 42. Each manual adjustment member 38 in addition to being displaceable along the length of the bow to move the piston 36, is also disengagable from shaft 42 so that it does not load power drive 40.

Also carried by each lens support 14, 16 is a lens focal length sensor which in this particular embodiment includes a solid state narrow band radiation source 50 on one side of the variable focus lens system and a compatible narrow band sensor 52 on the opposite side, the output of sensor 52 changing as a function of the quantity of liquid in chamber 30 and hence as the focal length of the lens system. Other focal length sensors may be used, as for example, sensing of the deflection of lens component 28.

Figure 2:
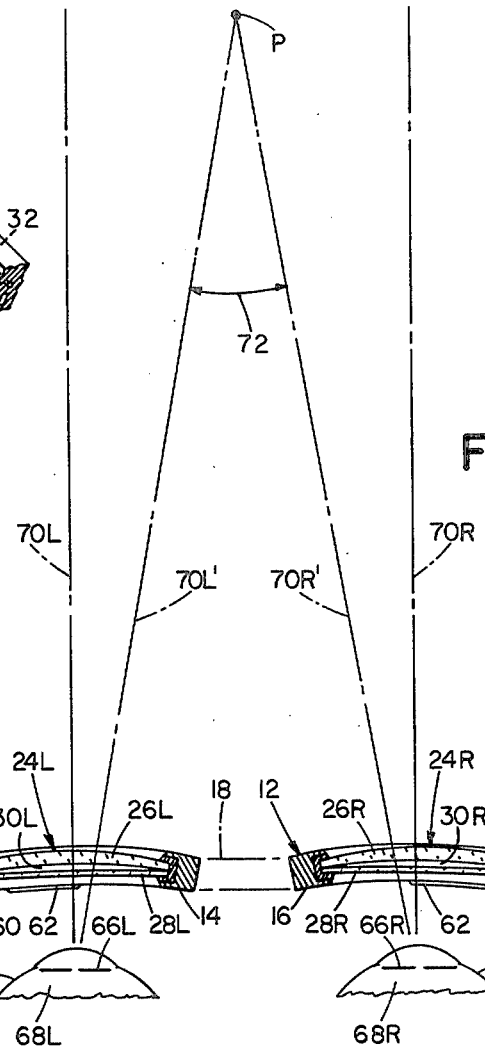
FIG. 2 is a diagrammatic top view of the vision corrective system of FIG. 1 showing the relation of the eyes of the wearer to the vision compensation system.
Figure 3:
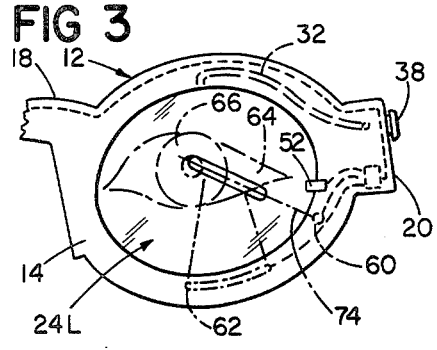
FIG. 3 is a diagrammatic view showing aspects of the eye position monitoring portion of the system shown in FIG. 1.

Each frame 14, 16 also carries an eye position sensing system that includes a solid state source of infrared radiation 60 and an extended sensor array 62. The eye position sensing system senses the position of the junction between sclera 64 (the white of the eye) and the iris 66 (which is invariably darker than the sclera). Each eye ball 68 is rotated in its orbital socket by ocular muscles. Corresponding ocular muscles acting in unison turn the eye balls 68 in the same direction while opposite ocular muscles acting in unison rotate the eye balls 68 in opposite directions. Thus, with reference to FIG. 2, the viewing axes 70 of eyes 68 are essentially parallel when viewing a distant object P and converge (as indicated at 70') when viewing a close object (and define a vergence angle 72). Each eye position sensing system monitors the position of the eye ball 68 in terms of reflections from the sclera 64 and iris 66 respectively as sensed by the sensor array 62. In the embodiment shown in FIGS. 1–3, a narrowly focused beam of weak infrared radiation is emitted by each light emitting diode 60 and extends along axis 74 across the junction between the sclera and the iris. The focused sensor array 62 monitors reflected radiation from the illuminated iris-sclera region and provides output signals that change as the position of the junction between sclera 64 and iris 66 changes, and thus indicates the angular position of the eye ball 68 being sensed. The outputs of the two sensor arrays 62 are compared and a resulting signal is produced which indicates the vergence angle 72 of the two eyes. The sensed shifts in the positions of the sclera-iris junctions correspond to distances of objects being viewed.

Depending on the nature of factors such as system configuration, hardware implementation and power source components may be mounted in the spectacle frame system itself or located away from the frame system and connected thereto by electrical conductors for example.

Figure 4:
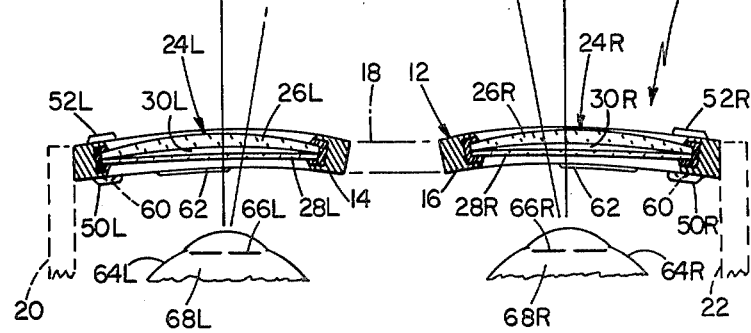
FIG. 4 is a block diagram of circuitry used in an embodiment of the system shown in FIG. 1.
Figure 4:
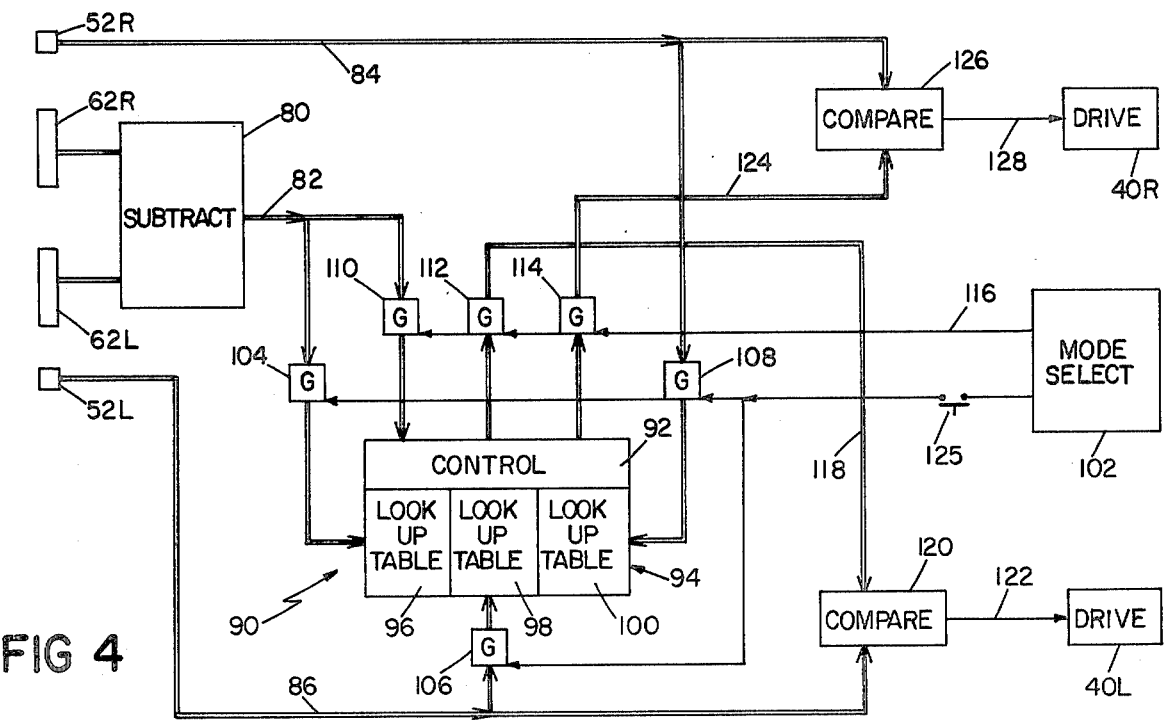

The signal processing circuitry shown in FIG. 4 includes subtractor circuitry 80 that responds to signals from sensor arrays 62L and 62R and produce an eye vergence angle signal on line 82. Lens sensors 52R and 52L similarly produce focal length signals on lines 84 and 86 respectively. Signal processor 90 includes a control section 92 and a memory 94 arranged to store three corresponding sets of data words—a first bank 96 that stores vergence angle signals, a second bank 98 that stores corresponding focal length signals from lens sensor 52L and a third bank 100 that stores corresponding focal length signals from lens sensor 52R. Mode select circuit 102 and gates 104–114 control transfer of data words to and from memory banks 96, 98 and 100. In a manual or input mode, eye vergence angle signals are applied through gate 104 for storage in lookup table 96 of memory 94 under the control of controller section 92, and focal length signals on lines 86 and 84 are applied through gates 106 and 108 for storage in corresponding storage registers of lookup tables 98 and 100. In the automatic or readout mode, mode select control 102 provides a signal on line 116 which conditions gates 110, 112 and 114. In that readout mode, a data word register in each of tables 98 and 100 is selected by identifying the corresponding register in table 96 whose data word is the same or most closely corresponds to the vergence angle signal passed by gate 110. The selected focal length output signal from table 98 is passed by gate 112 on line 118 for application to compare circuit 120 whose output on line 122 operates drive 40L. The drive signal on line 122 is determined by the relative values of the signals on lines 86 and 118 and the drive signal on line 122 terminates when the input signals 86, 118 compare satisfactorily. Drive signal 122 operates drive 40L to flow working fluid to or from chamber 30L to change the lens focal length which is sensed by sensor 52L. When the lens has been driven to the indicated position, the actual lens focal length output of sensor 52L, as applied over line 86, properly compares with the desired lens focal length signal on line 118 and drive 40L is deenergized. Similarly and concurrently a corresponding desired focal length signal for the right lens 24R is passed by gate 114 on line 124 and applied to compare circuit 126 for comparison with the actual focal length signal on line 84. The output of compare circuit 126 on line 128 similarly operates lens drive 40R. It will be apparent that separate similar controllers may be used for each lens system, and that all or portions of such controllers may be housed in the spectacle structures as indicated in FIG. 1.

In operation, each lens spectacle system is initially set in the manual mode and calibrated for the user with reference to a series of objects located at different distances. With respect to each object, the user manually adjusts the focus of each lens 24 with corresponding control 38 until a satisfactory focus is obtained. While the user is looking at the object with both lenses satisfactorily focused, input control 125 is operated to store the eye vergence angle signal on line 82 in a register in lookup table 96 and the lens focus signals on lines 84 and 86 are simultaneously stored in the corresponding registers in memory sections 98 and 100. This sequence is repeated for objects at a series of different distances, each with adjustment of the lenses and then storage of the vergence angle and focal length signals simultaneously in corresponding registers to establish a correlated data table in memory 94.

When this data table has been compiled, mode select control 102 is placed in automatic mode, deenergizing the manual control gates 104-108 and applying a signal on line 116 to condition gates 110-114.

In automatic mode, the eye vergence angle signal on line 82 is continuously applied to control 92 and periodically compared with the contents of registers in section 96. The data words in the registers in tables 98 and 100 corresponding to the register in table 96 that stores the data word most closely related to the eye vergence signal on line 82 are applied through gates 112 and 114 on lines 118 and 124 to compare circuits 120 and 126. If the desired focal length signal on line 118 differs from the actual focal length signal on line 86, compare circuit 120 has an output on line 122 which operates drive 40L in the desired direction to change the focal length of the controlled lens system 24L. Compare circuit 126 similarly controls lens system 24R. Thus, the vision compensation system operates automatically to bring the focal lengths of the lenses to values corresponding to the distance of the object then being viewed by the user as indicated by the eye vergence angle signal on line 82 in a system in which compensation calibration is easily accomplished directly for the user, and in which vergence angle signals and focal length signals are generated directly and with accurate correlation.

Another embodiment is shown in FIG. 5 in which two field of view photosensors 130, 132 are used with each eye 68'. Each photosensor 130, 132 is directed generally to the junction 134 between iris and sclera and each output changes as each eye ball rotates in a horizontal plane. The resulting signals on lines 136 are applied to differential amplifiers 138, each of which provides an output on line 140 of magnitude proportional to the eye angle. The eye angle voltages are applied to difference amplifier 142 whose output signal on line 144 indicates the vergence angle of the eyes. A compensation factor (as a function of the interocular distance D) may be inserted through use of divider circuit 146. The resulting signal on line 148 is supplied to analog function generator 150 whose outputs on lines 152 are a function of the input signal on line 148 such that increasing focal length demands decreasing volume of working liquid. The signals on each line 152 are applied through power amplifier 154 to the pump drive 156 to change the volume of working liquid in the lens system to the desired value. A calibrated plunger can be used in open loop mode. If desired, the lens control system may be of the closed loop type and employ a focal length sensor that, for example, includes emitter 160 and sensor 162, sensor 162 providing a focal length signal on line 164 that is supplied to function generator 166 to generate a reference volume signal on line 168 for application to power amplifier 154. Automatic compensation for environmental changes, as for example, changes in external pressure resulting from altitude changes or atmosphere changes in barometric pressure may also be incorporated in either type of control.

While particular embodiments of the invention have been shown and described, various modifications thereof will be apparent to those skilled in the art and therefore it is not intended that the invention be limited to the disclosed embodiments or details thereof and departures may be made therefrom within the spirit and scope of the invention as defined in the claims.

What is claimed is:

1. A vision compensation system comprising a support frame adapted for wearing by a user, said frame carrying at least one optical member with a variable optical characteristic, means including sensor means carried by said frame for producing an eye position signal as a function of the relative angular positions of the eyes of the wearer and means responsive to said eye position signal for changing the variable optical characteristic of said one optical member to provide compensation for impaired accommodative capacity of the wearer's eye.

2. The system according to claim 1 and further including adjusting means manipulatable by the fingers of the wearer while the vision compensation system is being worn for changing said variable optical characteristic of said one optical member.

3. The system according to claim 1 and further including means carried by said lens support frame for sensing the variable optical characteristic of said one optical member and providing an optical member characteristic signal and feedback means responsive to said optical member characteristic signal for adjusting said one optical member.

4. The system according to claim 1 wherein said frame carries radiation sources for illuminating the eyes of the wearer, and sensor arrays tuned to the radiation wavelength of said sources for providing eye position signals as a function of the angular positions of the iris-sclera junctions of the eyes of the wearer.

5. The system according to claim 1 wherein said eye position signal responsive means includes compare circuitry responsive to actual optical member characteristic signals and desired optical member characteristic signals for producing a optical member characteristic control signal.

6. The system according to claim 5 wherein said compare circuitry includes a power amplifier.

7. The system according to claim 1 wherein said eye position signal responsive means includes a control system having a first function generator responsive to a vergence angle signal for generating a desired optical member characteristic signal and a second function generator for generating an actual optical member characteristic signal.

8. The system according to claim 1 wherein said eye position signal responsive means includes a control system having a calibration mode and an automatic mode,
circuitry responsive to said sensor means for producing vergence angle signals,
memory means for storing correlated vergence angle signals and optical member characteristic signals when said control system is in said calibration mode, and
selection means operative when said control system is in said automatic mode for selecting lens characteristic signals in said memory as a function of changing vergence angle signals to control the variable optical characteristic of said one optical member.

9. A vision compensation system comprising a support frame adapted for wearing by a user, said frame carrying at least one optical member that includes two lens elements spaced to define a chamber therebetween, means including sensor means carried by said frame for producing an eye position signal as a function of the relative angular positions of the eyes of the wearer and means responsive to said eye position signal for transferring a working fluid to and from said chamber for changing the focal length of said one optical member to provide compensation for impaired accommodative capacity of the wearer's eye.

10. A vision compensation system comprising a support frame of conventional spectacle configuration adapted for wearing by a user, said frame carrying two separate lens systems, each having a variable focal length capability, means including sensor means carried by said frame for producing an eye position signal as a function of the relative angular positions of the eyes of the wearer and means responsive to said eye position signal for changing the focal length of at least one of said lens systems to provide compensation for impaired accommodative capacity of the wearer's eye.

11. The system according to claim 10 and further including lens sensors carried by said frame for providing signals indicating actual focal length settings of said two separate lens systems.

12. The system according to claim 11 wherein each said lens system includes two lens elements spaced to define a chamber therebetween and means for transferring a working fluid to and from said chamber to change the focal length of that lens system.

13. The system according to claim 12 wherein said eye position signal responsive means includes a control system having a calibration mode and an automatic mode,
circuitry responsive to said sensor means for producing vergence angle signals,
memory means for storing correlated vergence angle signals and lens characteristic signals when said control system is in said calibration mode, and
selection means operative when said control systems in said automatic mode for selecting lens characteristic signals in said memory as a function of changing vergence angle signals to control the variable optical characteristic of said lens systems.

14. The system according to claim 12 wherein said eye position signal responsive means includes a control system having a first function generator responsive to a vergence angle signal for generating a desired lens characteristic signal and a second function generator for generating an actual lens characteristic signal.

15. The system according to claim 12 wherein said eye position signal responsive means includes compare circuitry responsive to actual lens characteristic signals and desired lens characteristic signals for producing a lens characteristic control signal.

16. The system according to claim 15 wherein said spectacle frame carries radiation sources for illuminating the eyes of the wearer, and sensor arrays tuned to the radiation wavelength of said sources for providing eye position signals as a function of the angular positions of the iris-sclera junctions of the eyes of the wearer.

* * * * *